(12) United States Patent
Ho

(10) Patent No.: US 7,762,254 B2
(45) Date of Patent: Jul. 27, 2010

(54) MASK MOUNTING MECHANISM

(75) Inventor: Peter Chi Fai Ho, Pittsburgh, PA (US)

(73) Assignee: RIC Investments, LLC, Wilmington, DE (US)

( * ) Notice: Subject to any disclaimer, the term of this patent is extended or adjusted under 35 U.S.C. 154(b) by 1031 days.

(21) Appl. No.: 11/496,114

(22) Filed: Jul. 31, 2006

(65) Prior Publication Data

US 2007/0028919 A1 Feb. 8, 2007

Related U.S. Application Data

(60) Provisional application No. 60/704,688, filed on Aug. 2, 2005.

(51) Int. Cl.
*A61M 11/00* (2006.01)

(52) U.S. Cl. ............... 128/205.25; 128/204.18; 128/206.26; 128/207.11

(58) Field of Classification Search ............ 128/205.25, 128/206.21, 206.26, 207.11, 207.17, 204.18, 128/200.14–200.24
See application file for complete search history.

(56) References Cited

U.S. PATENT DOCUMENTS

| | | | |
|---|---|---|---|
| 5,644,795 A | 7/1997 | Landis | |
| 5,662,101 A | 9/1997 | Ogden et al. | |
| 5,884,624 A | 3/1999 | Barnett et al. | |
| 6,397,847 B1 | 6/2002 | Scarberry et al. | |
| 6,412,488 B1 | 7/2002 | Barnett et al. | |
| 6,516,802 B2 | 2/2003 | Hansen et al. | |
| 6,595,214 B1 | 7/2003 | Hecker et al. | |
| 6,631,718 B1 | 10/2003 | Lovell | |
| 6,823,869 B2 | 11/2004 | Raje et al. | |
| 2003/0145859 A1 | 8/2003 | Bohn | |
| 2004/0045551 A1 | 3/2004 | Eaton et al. | |
| 2004/0112387 A1 | 6/2004 | Lang | |
| 2006/0201514 A1* | 9/2006 | Jones et al. ............ | 128/206.21 |

OTHER PUBLICATIONS

PCT Search Report and Written Opinion, Feb. 27, 2007.

* cited by examiner

*Primary Examiner*—Steven O Douglas
(74) *Attorney, Agent, or Firm*—Michael W. Haas

(57) ABSTRACT

A mask mounting mechanism for use in connection with a patient interface device having a mask and a mask attachment assembly with at least one strap for retaining the mask in a sealed position on a user's face. The mask mounting mechanism includes a button element extending from the mask, and the button element includes a shaft and a cap having a diameter greater than the diameter of the shaft. A clip element includes a clip element arm and a buckle. A second end of the arm includes an orifice extending therethrough. The buckle is attached to a first end of the clip element arm for engaging the strap of the mask attachment assembly. The clip element is engageable with a button element by engaging the orifice of the clip element arm over the cap and adjacent the shaft of the button element.

20 Claims, 10 Drawing Sheets

MASK MOUNTING MECHANISM

CROSS-REFERENCE TO RELATED APPLICATIONS

This application claims priority under 35 U.S.C. §119(e) from provisional U.S. Patent Application No. 60/704,688 filed Aug. 2, 2005 the contents of which are incorporated herein by reference.

BACKGROUND OF THE INVENTION

1. Field of the Invention

The present invention relates generally to structures and assemblies for use in connection with a patient interface device, such as a respiratory mask, and a mask attachment assembly, such as a headgear having straps to retain the mask in a sealed position on a user's face. In particular, the present invention relates to a mask mounting mechanism connected to the respiratory mask and providing an attachable and detachable buckle and a clip element that is continuously rotatable around a button element, thereby providing additional convenience, ease-of-use, ease-of-adjustment and removal and improved comfort to the patient.

2. Description of the Related Art

It is well known to treat a medical disorder or to diagnose, treat or monitor the condition of the patient using medical equipment. For example, a patient may be monitored and treated for various sleep disorders in a lab or in some other setting. One such sleep disorder is sleep apnea. Obstructive sleep apnea is characterized by a collapse of the upper airways during sleep, while central sleep apnea is characterized by the suspension of all respiratory movement. Obstructive sleep apnea and central sleep apnea may be combined in a condition referred to as mixed apnea.

In order to diagnose and/or treat such medical disorders, various equipment and devices are required for successfully diagnosing and prescribing treatment. Further, there are numerous situations where it is necessary or desirable to deliver a flow of breathing gas, non-invasively, to the airway of a patient, i.e., without intubating the patient or surgically inserting a tracheotomy tube in their trachea. For example, it is known to ventilate a patient using a technique known as non-invasive ventilation. It is also known to deliver continuous positive airway pressure (CPAP) or variable airway pressure, which varies with the patient's respiratory cycle or a monitored condition of the patient, to treat a medical disorder, such as sleep apnea syndrome, in particular, obstructive sleep apnea (OSA), congestive heart failure, stroke, Cheynes-Stokes respiration, etc. Non-invasive ventilation and pressure support therapies involve the placement of a patient interface device, which is typically a nasal or nasal/oral mask, on the face of a patient to interface the ventilator or pressure support device with the airway of the patient, so that a flow of breathing gas can be delivered from the pressure/flow generating device to the airway of the patient.

Patients suffering from a pulmonary or respiratory disorder, such as obstructive sleep apnea, are often treated with a pressure support device, such as a continuous positive airway pressure (CPAP) device. A CPAP device delivers a flow of fluid to the airway of the patient throughout the patient's breathing cycle in order to "splint" the airway open, thereby preventing its collapse during sleep. In another type of treatment, bi-level positive pressure therapy is provided to the patient, in which the pressure of air delivered to the patient's airway varies or is synchronized with the patient's breathing cycle to maximize therapeutic effect and comfort to the patient. A pressure support device may also provide "bi-level" pressure support, in which a lower pressure is delivered to the patient during the patient's expiratory phase then during the inspiratory phase.

It is also known to provide an auto-titration positive pressure therapy in which the pressure provided to the patient changes based upon the detected conditions of the patient, such as whether the patient is snoring or experiencing an apnea, hypopnea, or upper airway resistance. Such a device adjusts the pressure delivered to the patient, based on whether or not the patient is snoring. For example, a pressure support device may actively test the patient's airway to determine whether obstruction, complete or partial, could occur and adjust the pressure output to avoid this result.

Other modes of providing positive pressure support to a patient are known. For example, a proportional assist ventilation mode of pressure support provides a positive pressure therapy in which the pressure of gas delivered to the patient varies with the patient's breathing effort to increase the comfort of the patient. Proportional positive airway pressure (PPAP) devices deliver breathing gas to the patient based on the flow generated by the patient.

For purposes of the present invention, the phrase "pressure support system", "pressure support device", or "positive pressure support" includes any medical device or method that delivers a flow of breathing gas to the airway of a patient, including a ventilator, CPAP, bi-level, PAV, PPAP, or bi-level pressure support system.

Typically, gas such as oxygen or air is delivered by a pressure generating device, which may be, in turn, in fluid communication with an oxygen tank. The oxygen flows from the source through the regulator devices, through the pressure generating device and further through a conduit into a patient interface. The pressure generating device and the conduit, such as a gas hose, are considered the patient circuit, such that a coupling assembly is required for connecting the patient circuit to the patient interface device.

In a conventional pressure support system, a flexible conduit is coupled to an exit conduit from the pressure generating device. The flexible conduit forms part of the patient circuit that carries the flow of breathing gas from the pressure generating system to the patient interface device. In a support system, the patient interface device connects the patient circuit with the airway of the patient so that the elevated pressure gas flow is delivered to the patient's airway.

In order to provide gas or, as discussed above, oxygen, to a patient, the patient must use a patient interface device, such as a nasal mask (including external cushions and/or internal prongs), nasal/oral mask, full-face mask, nasal cannula, oral mouthpiece, tracheal tube, endotracheal tube, or hood. Typically, patient interface devices include a mask shell having a cushion attached to the shell that contacts the surface of the patient. The mask shell and cushion are held in place by a headgear that wraps around the head of the patient. Together, the mask and headgear form the patient interface assembly. A typical mask attachment assembly includes headgear having flexible, adjustable straps that extend from the mask to attach the mask to the patient. Other techniques for attaching a patient interface device use a vice-like device that anchors at the front and back of the patient's head to support the mask on the user. See, e.g., U.S. Pat. No. 6,516,802.

Because such patient interface devices are typically worn for an extended period of time, a variety of concerns must be taken into consideration. For example, in providing CPAP or other positive pressure therapy to treat OSA, the patient normally wears the patient interface device all night long while he or she sleeps. In order to be successful in these applications, a patient interface needs to take into account two, often competing, goals: comfort and technical effectiveness. Failure to achieve either goal is likely to result in low efficacy. A comfortable, but technically ineffective, patient interface may achieve superior patient compliance; however, its technical ineffectiveness will minimize the therapeutic benefit achieved. Alternatively, a technically effective, but uncomfortable, patient interface may be capable of treating a patient; yet, the lack of comfort often results in low patient compliance. This also undermines the ultimate therapeutic benefit obtained by the patient. Thus, further advancements for interfacing a pressure support system to the airway of a patient are desired.

It is known to maintain such interface devices on the face of a wearer with a headgear assembly having upper and lower straps, each having opposite ends threaded through connecting elements provided on the opposite sides and top of the interface device, such as a mask. Because such masks are typically worn for an extended period of time, it is important that the headgear maintain the mask with a tight enough seal against a patient's face while minimizing discomfort. Adjustability of the mask and/or the headgear, together with increased patient comfort, is significant. However, most important is the maintenance of the seal between the mask and the user's face. According to the prior art, various headgear have been developed that position the straps in various locations with respect to the mask in order to effect this seal.

According to the prior art, various embodiments of collars and mask assemblies that allow for the variable positioning of headgear straps have been provided. For example, U.S. Pat. No. 6,412,488 to Barnett et al. discloses a collar 34 that is attachable to the mask with multiple cutouts 84 for attaching the strap of a mask thereto. Another collar device for attachment to a mask, and to allow variable positioning, is disclosed in U.S. Pat. No. 5,662,101 to Ogden et al. The Ogden assembly includes a rigid plate 9 connected to a facial mask assembly 1. Straps, such as adjustable straps 13R, 13L are inserted through the openings 29, 31 in order to secure the mask assembly 1 in a sealed position against the user's face. However, the devices of the Barnett patent and the Ogden patent, while moveable between various positions, are not fully flexible, rotatable or easily attachable and detachable to the mask.

Yet another mask mounting mechanism or collar according to the prior art is shown and described in U.S. Pat. No. 6,631,718 to Lovell, which is similar in design and operation to the Barnett device. In particular, the Lovell device includes a retainer 12, 212 that is attachable to the shell 4 of the mask. This retainer, 12, 212 includes lower connection points 14, 214 and at least one upper connection point 16, 216, as best illustrated in FIGS. 1, 2A, 7 and 9-11. While, like the Barnett device, the assembly of the Lovell patent permits multiple attachment points for variations in strap connection and positioning, the retainer 12, 212 is not rotatable about the shell 4 of the mask. Accordingly, the Lovell device is not rotatable, and does not provide flexibility in attachment. In addition, the Lovell device does not provide for the simple attachment and removal of the buckle (and, hence, the strap) to and from the mask. A similar non-rotatable and inflexible headgear/strap assembly is disclosed in U.S. Pat. No. 6,823,869 to Raje et al., such as in, e.g., FIGS. A11 and F36.

Yet another mask mounting mechanism according to the prior art is disclosed in U.S. Pat. No. 6,595,214 to Hecker et al. The Hecker et al. patent discloses a clip element in the form of an eyelet 7 extending from a mask 1 is disclosed. The Hecker mask illustrates that, as opposed to a collar attached to the mask, individual clip elements, each with a buckle or eyelet 7 thereon, can be directly attached to the mask shell. As discussed above in connection with the collar devices, the eyelets 7 (or clip elements) of the Hecker patent are permanently affixed to the mask. Accordingly, these clip elements are non-rotatable and illustrate an inflexible strap attachment assembly. In addition, it is difficult to maintain an adequate seal in these devices.

SUMMARY OF THE INVENTION

Accordingly, it is an object of the present invention to provide a mask mounting mechanism that addresses one or more of the above-identified concerns and overcomes the shortcomings of conventional mask mounting assemblies, masks, headgear and the like in the gas delivery art. In accordance with the broad teachings of the present invention, a mask mounting mechanism, system and patient interface device are provided.

In particular, the mask mounting mechanism of the present invention is for use in connection with a patient interface device having a mask and a mask attachment assembly. The mask attachment assembly includes at least one, and typically multiple straps, for retaining the mask in a sealed position on a user's face. The mask mounting mechanism includes a button element extending from a wall of the mask, and this button element includes a shaft and a cap having a diameter greater than the diameter of the shaft. The mask attachment mechanism also includes a clip element having a clip element arm and a buckle. The clip element arm includes a first end and a second end with an orifice extending therethrough. The buckle is attached to the first end of the clip element arm and adapted to engage a strap of the mask attachment assembly. The clip element is engageable with the button element by engaging the orifice of the clip element arm over the cap and adjacent the shaft of the button element. The clip element is continuously rotatable around the shaft of the button element.

The present invention is further directed to a patient interface device, including: a mask having a mask wall with a mask port extending therethrough; a mask conduit coupling in fluid communication with the mask port; and a mask attachment assembly having at least one strap for retaining the mask in a sealed position on a user's face. The device further includes a mask mounting mechanism, including a clip element having a clip element arm and a buckle. The clip element arm includes a first end and a second end with an orifice extending therethrough. The buckle is attached to the first end of the clip element arm and adapted to engage a strap of the mask attachment assembly. The clip element is engageable with the button element by engaging the orifice of the clip element arm over the cap and adjacent the shaft of the button element. The clip element is continuously rotatable around the shaft of the button element.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DETAILED DESCRIPTION OF THE EXEMPLARY EMBODIMENTS

Figure 1:
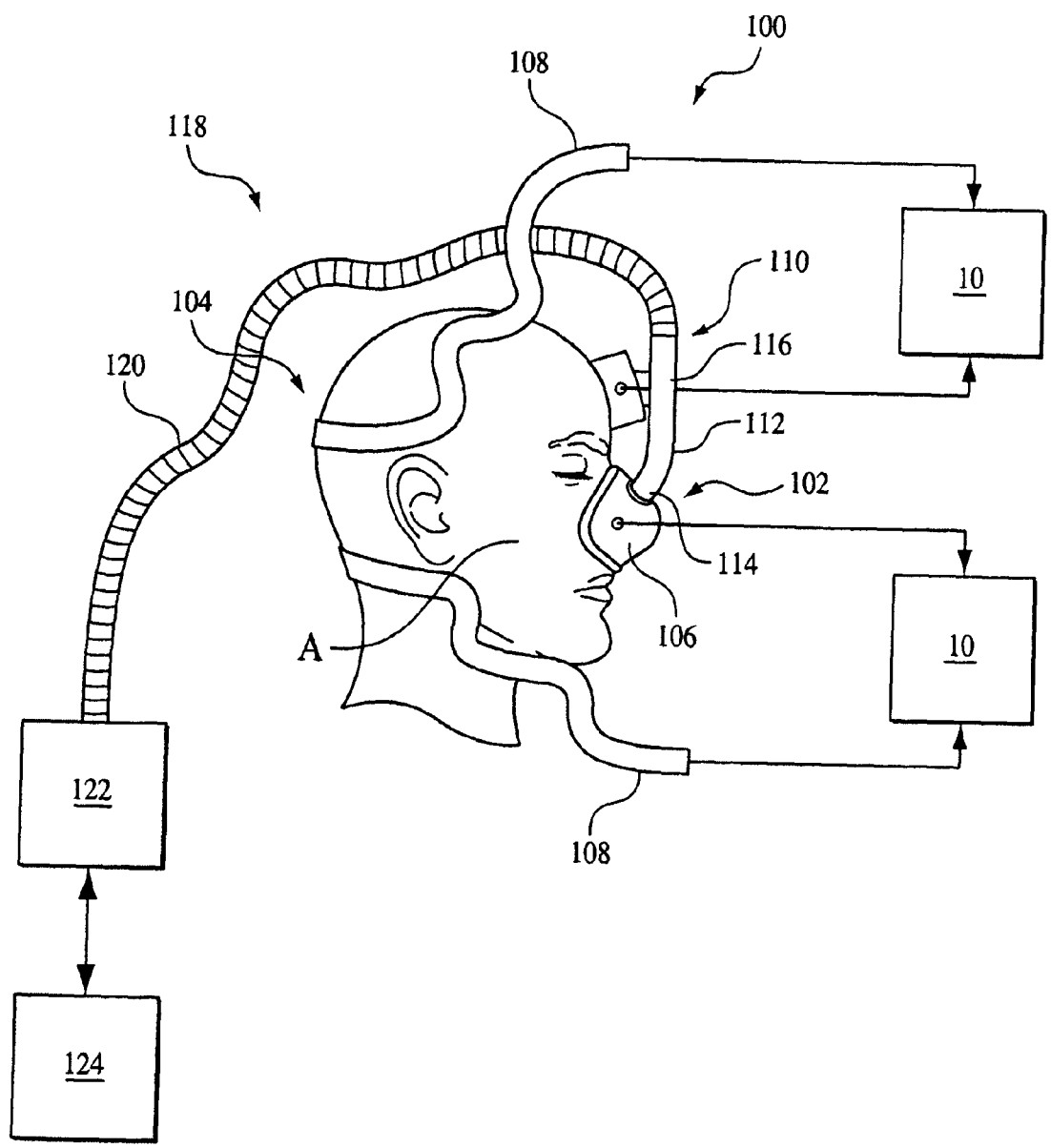
FIG. 1 is a schematic view of a mask mounting mechanism according to the principles of the present invention for use in connection with a patient interface device having a mask attachment assembly.

The present invention is directed to a mask mounting mechanism 10 as illustrated in various embodiments in FIGS. 1-10, and in use in connection with a user's face A in FIG. 1. In particular, and as illustrated in schematic form in FIG. 1, the mask mounting mechanism 10 is designed to be used in connection with a patient interface device 100, which includes a mask 102 and a mask attachment assembly 104. The mask 102 can be a nasal mask (including an external cushion and/or internal prongs), an oral mask, a nasal and oral mask, a full-face mask or other similar devices and structures as are known in the art. In addition, the mask mounting mechanism 10 of the present invention can be used in connection with any of the components and subcomponents of the patient interface device 100. The mask 102 includes a mask port (not shown) extending through a mask wall 106. The mask port allows gas, such as oxygen, air and the like, to flow through the mask port and into the mask 102 for inhalation by the patient.

The mask attachment assembly 104 includes at least one, and typically multiple straps 108 for retaining the mask 102 in a sealed position with respect to the user's face A. One advantage of the mask mounting mechanism 10 of the present invention is that it can be used in connection with many different types and variations of mask attachment assemblies 104 and headgear with straps 108. For example, the mask mounting mechanism 10 can be used in connection with a three-point attachment assembly, a four-point attachment assembly, a vertically-oriented attachment assembly, a horizontally-oriented attachment assembly, and any of these assemblies may include a number of straps 108 for securing the mask 102 against the user's face A. In addition, and as is known in the art, the straps 108 can be adjustable with respect to the mask attachment assembly 104 and/or some associated headgear or retention device.

In one embodiment, the patient interface device 100 includes a forehead support assembly having a forehead contact member 110, which is attached to and extends from the mask 102. An example of one type of forehead support assembly is shown and described in U.S. Publication No. 2004/0045551, which has been assigned to the Assignee of the present invention and incorporated herein by reference. At least a portion of the forehead contact member 110 contacts a portion of a user's forehead. As is known in the art, the forehead contact member 110 may include a padded element for comfortably contacting the user's forehead. For example, the padded element can be a gel-filled cushion, such as a detachable gel-filled cushion, which is shown and described in U.S. Pat. Nos. 5,884,624 and 6,397,847, which have been assigned to the Assignee of the present invention and incorporated herein by reference.

In one embodiment, the patient interface device 100 includes a mask conduit coupling 112 in fluid communication with the mask port (not shown). In a further embodiment, the mask conduit coupling 112 includes a first end 114 and a second end 116, and the first end 114 of the mask conduit coupling 112 is attached to the mask 102. The second end 116 of the mask conduit coupling 112 is in fluid communication with a patient circuit 118, a conduit 120, a pressure support device 122, a gas source 124 or any combination thereof. The patient circuit 118 is an arrangement that is known in the art. In particular, the patient circuit 118 typically includes the conduit 120 in fluid communication with the pressure support device 122. In operation, the gas, typically oxygen or air, flows from the pressure support device 122, which may receive oxygen from an oxygen tank or other similar gas source 124, through the conduit 120, further through the mask conduit coupling 112 and the mask port and into the mask 102, as discussed above. In this manner, the patient receives gas delivery for inhalation.

Figure 2:
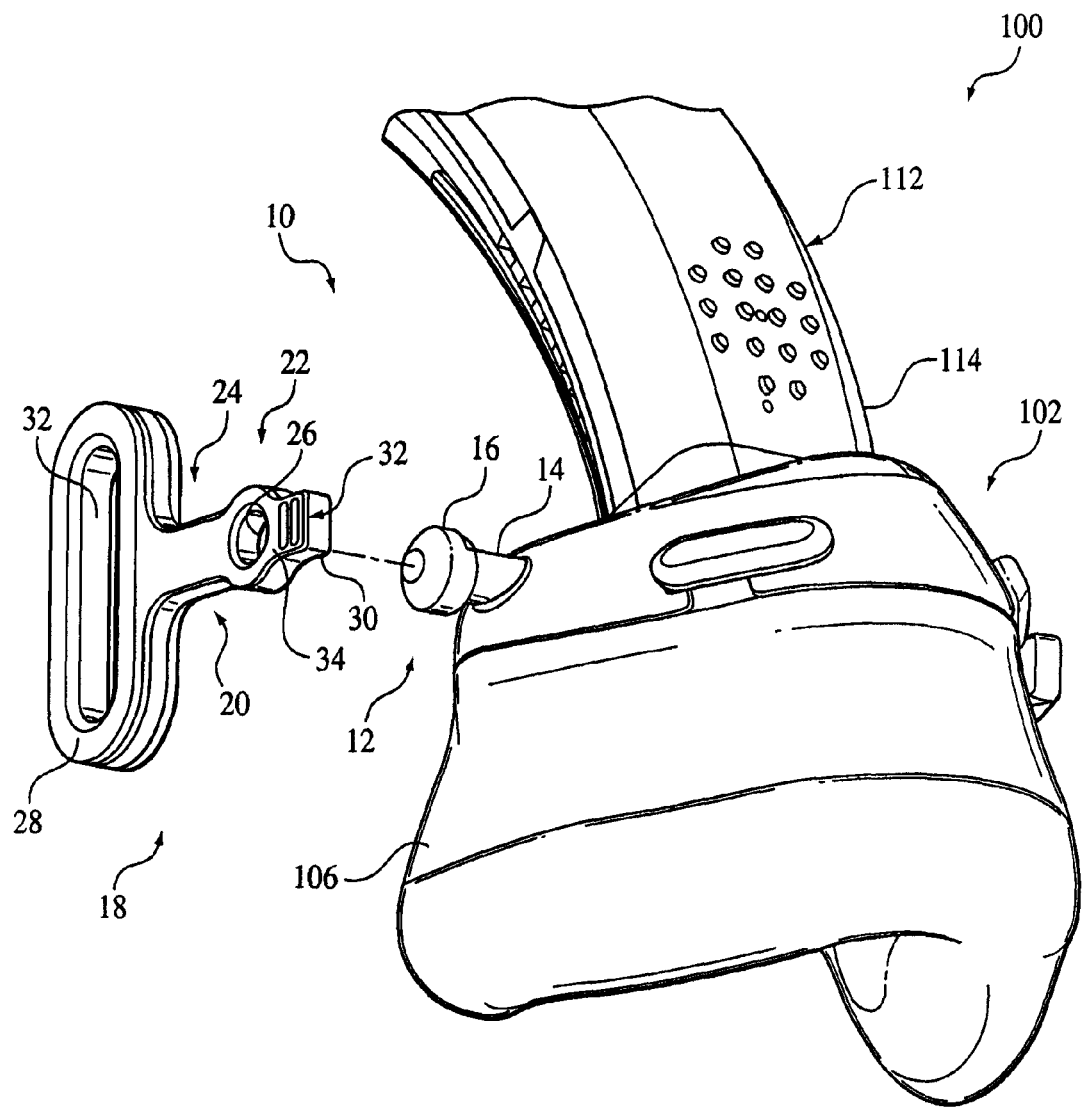
FIG. 2 is an exploded perspective view of a mask mounting mechanism according to the principles of the present invention, depicting a clip element of the mask mounting mechanism exploded from a button element of the mask mounting mechanism.

With respect to the present invention, and as seen in schematic form in FIG. 2, the mask mounting mechanism 10 includes a button element 12 extending from the mask wall 106. The button element 12 includes a shaft 14 and a cap 16. In particular, the cap 16 has a diameter greater than the diameter of the shaft 14. The mask mounting mechanism 10 also includes a clip element 18. The clip element 18 includes a clip element arm 20 with a first end 22 and a second end 24. The second end 24 of the clip element arm 20 includes an orifice 26 extending therethrough.

The clip element 18 further includes a buckle 28, which is attached to the first end 22 of the clip element arm 20. This buckle 28 is used to engage one or more of the straps 108 of the mask attachment assembly 104. Specifically, a buckle orifice 52 extends through and forms the buckle 28, such that a strap 108 is attachable through the buckle orifice 52, as is known in the art.

In operation, the clip element 18 is engageable with the button element 12 by engaging the orifice 26 of the clip element arm 20 over the cap 16 and adjacent the shaft 14 of the button element 12. Once engaged, the clip element 18 is continuously rotatable around the shaft 14 of the button element 12. It is this rotatability that allows the clip element 18 to be used in conjunction with a variety of different mask attachment assemblies 104 and straps 108, and effectively used regardless of the angular orientation and design of the straps 108.

Figure 3:
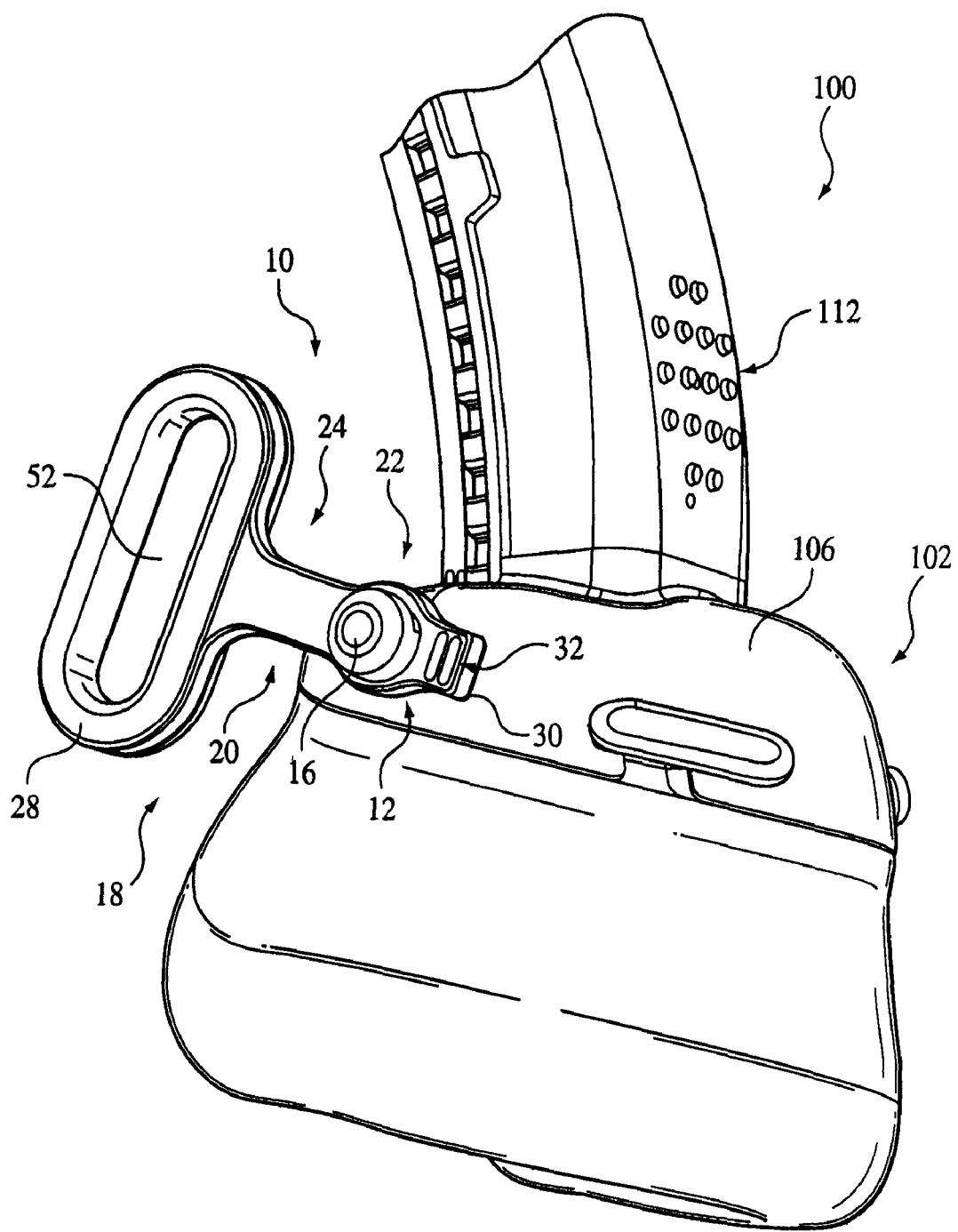
FIG. 3 is a perspective view of the mask mounting mechanism of FIG. 2, wherein the clip element is attached to the button element.
Figure 4:
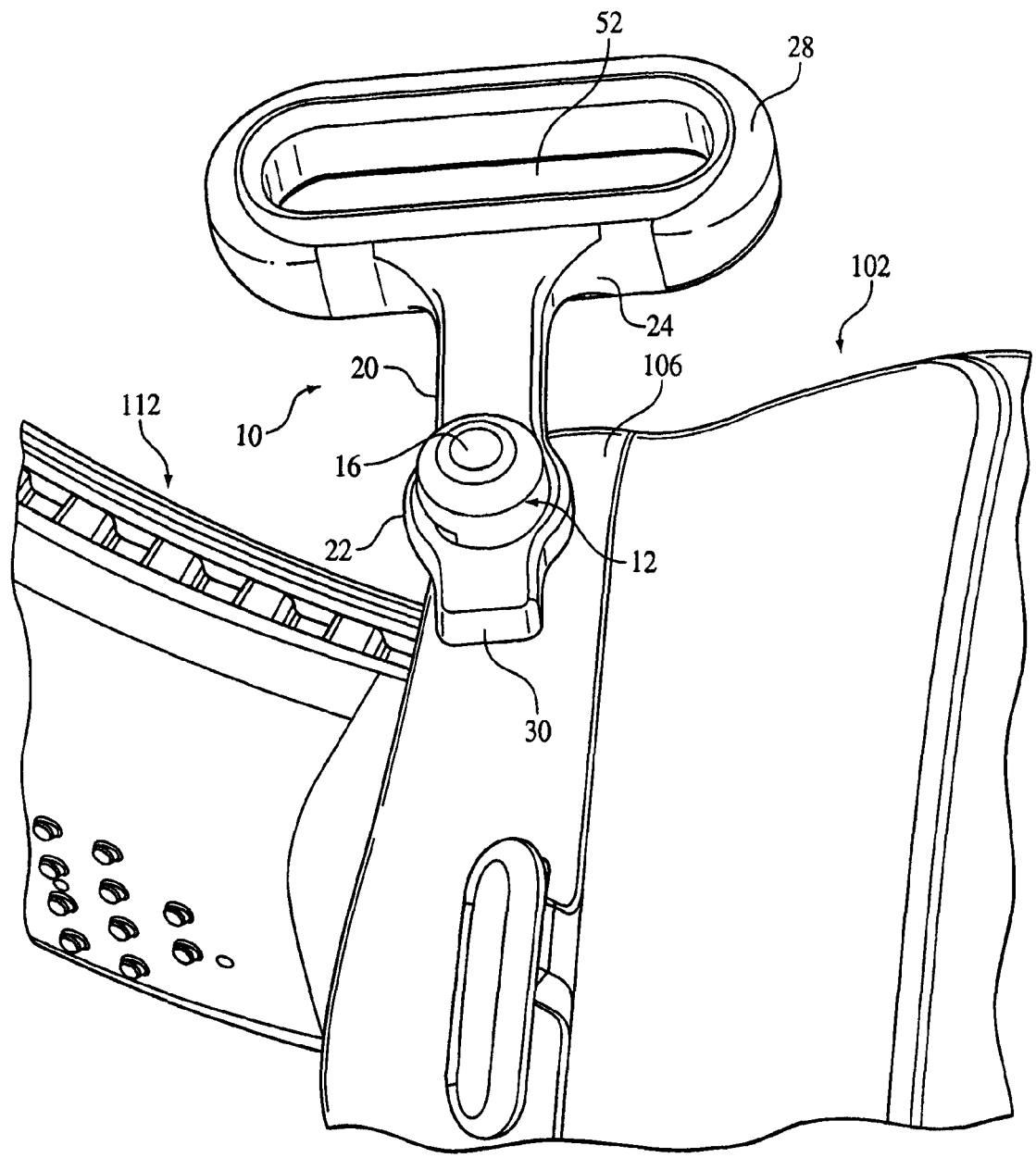
FIG. 4 is a magnified perspective view of the mask mounting mechanism of FIG. 3.

In one embodiment, and as best illustrated in FIGS. 2-4, a tab 30 extends from the second end 24 of the clip element arm 20. Tab 30 is provided to the user for grasping, such that the user may engage or grasp the tab 30 and disengage the clip element 18 from the button element 12.

As illustrated in FIGS. 2 and 3, the tab 30 also includes one, and typically multiple, ridges 32 extending from a surface 34 of the tab 30. These ridges 32 provide a gripping surface for the user to better grasp the tab 30. It is further envisioned that in the place of such ridges 32, grooves, bumps or other projections or recesses may be provided on the surface 34 of the tab 30 in order to provide an effective gripping surface to the user.

Figure 5:
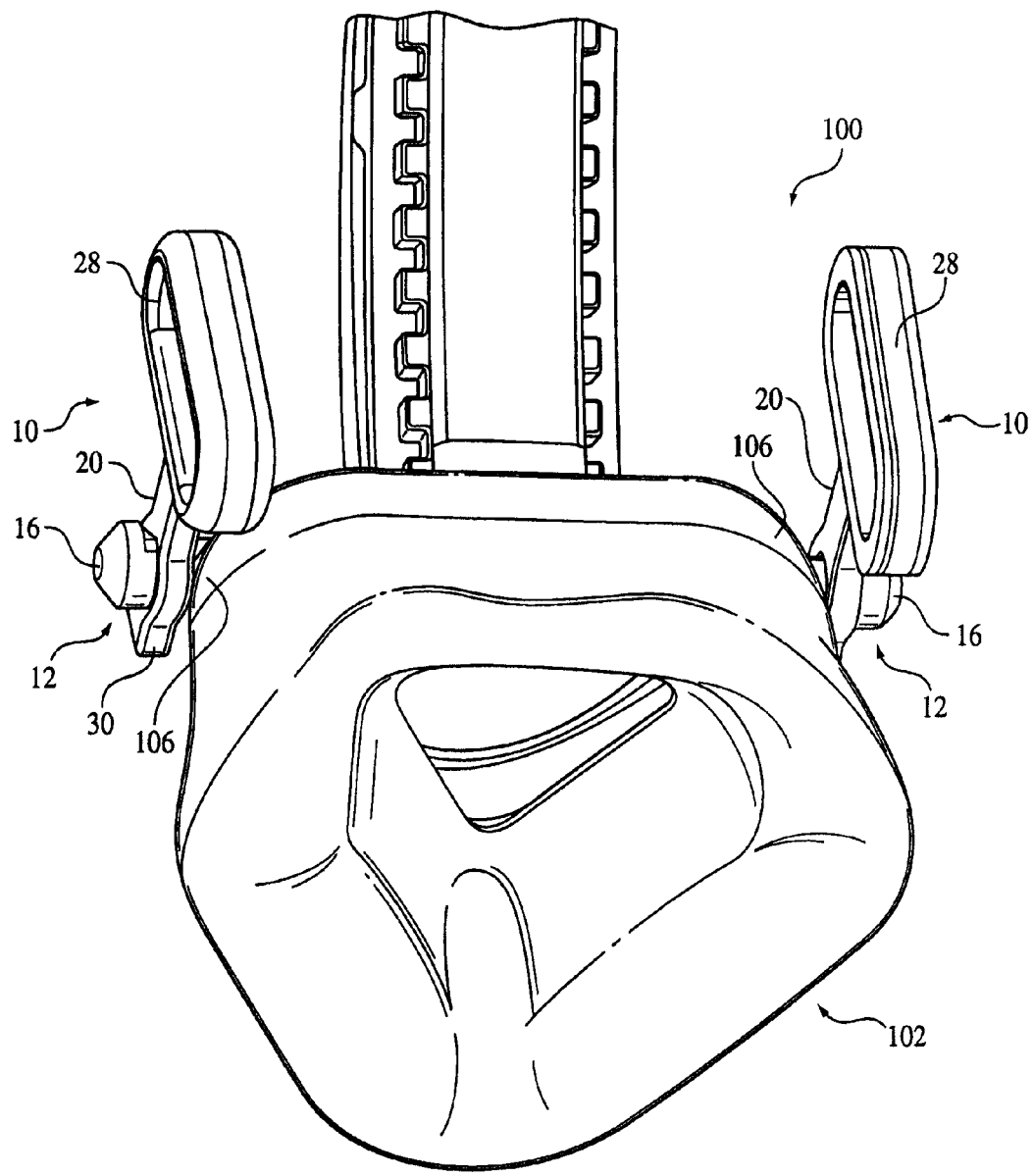
FIG. 5 is a perspective view of the mask mounting mechanisms according to the principles of the present invention in use in connection with a mask.
Figure 6:
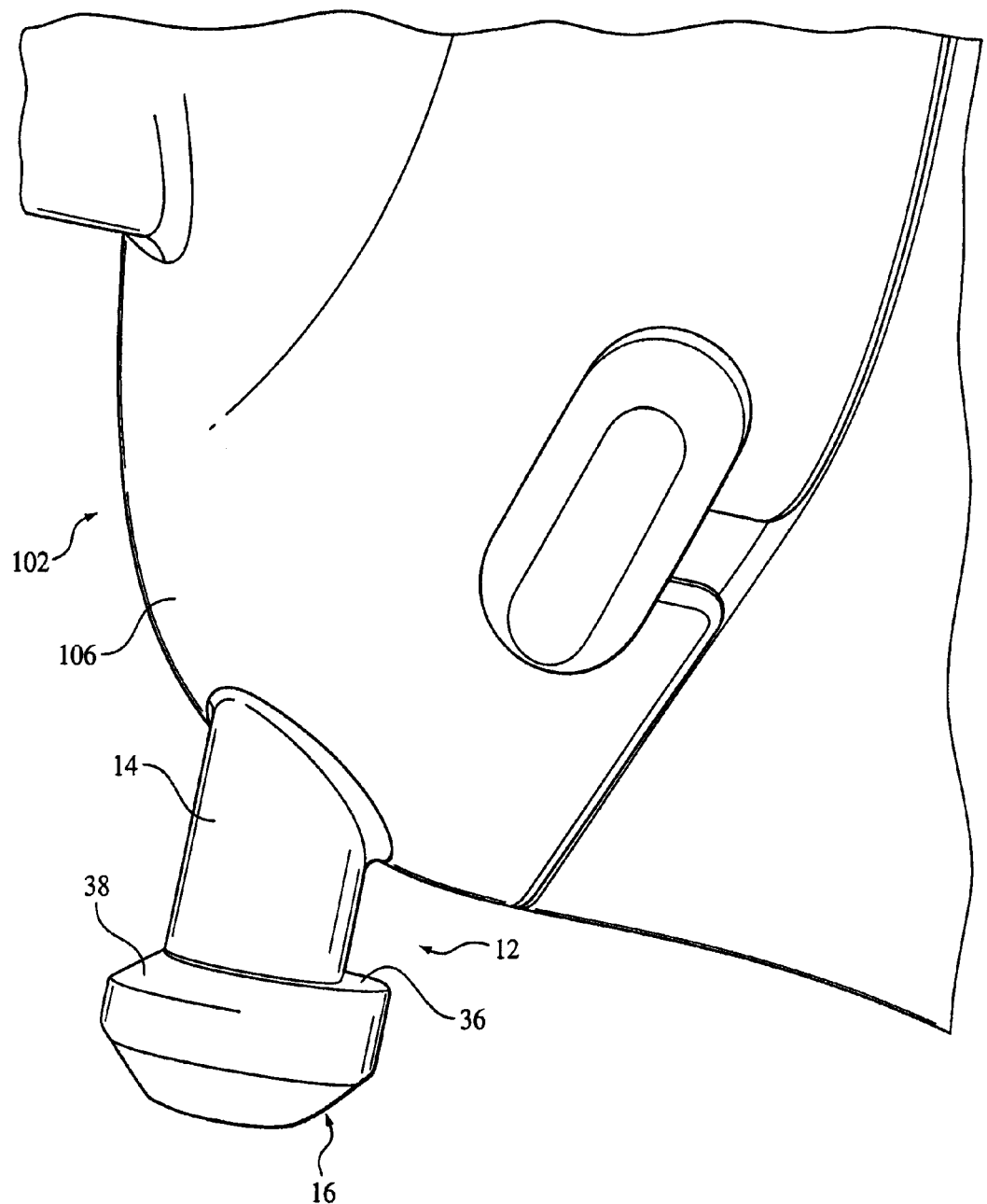
FIG. 6 is a magnified perspective view of one embodiment of a button element of the mask mounting mechanism according to the principles of the present invention.

As best seen in FIG. 6, the cap 16 of the button element 12 may be in a variety of forms, such as in the shape of a mushroom, a cone or any combination thereof. Of course, the cap 16 and the button element 12 may have a variety of geometries without departing from the scope of the present invention. In addition, in one embodiment, the cap 16 of the button element 12 includes a retention surface 36 for retaining the clip element arm 20 after engagement of the orifice 26 of the clip element arm 20 with the button element 12. Such engagement is seen in FIGS. 4 and 5, where it is illustrated that once the clip element 18 has been engaged with the button element 12, the width or diameter of the cap 16, as well as the width or diameter of the retention surface 36, are sufficient to retain the clip element arm 20 after attachment. However, the diameter of the orifice 26 of the clip element arm 20 is less than the diameter of the shaft 14, such that the clip element arm 20, and thus the clip element 18 and buckle 28, are fully rotatable about the shaft 14. This rotation provides the flexibility required for easy and convenient adjustment and removal, as well as various other benefits as can be best appreciated by one of ordinary skill in the art.

In one embodiment, at least a portion of the retention surface 36 of the cap 16 is tapered to simplify coupling and decoupling the clip element orifice 26 from around the shaft 14 and over the cap 16. Accordingly, a tapered surface 38 is provided, and as discussed in detail hereinafter with further embodiments, when used in connection with a flexible clip element arm 20, the tapered surface 38 allows a much easier removal of the clip element 18 from the button element 12.

The tapered surface 38 may be specifically positioned such that, in combination with the tab 30, the clip element 18 is easily removed only in a desired direction. For example, when a strap 108 is attached to the buckle 28, the resultant strapping force pivots the clip element arm 20 towards the user's face A. Such a position would ensure that the clip element 18 is not easily removed when appropriately engaged with the straps 108 due to the engagement of the surface 34 with retention surface 36. Therefore, the seal of the mask 102 against the user's face A would not be jeopardized. When it is desirable to remove clip element 18, the clip element is pivoted approximately 90 degrees such that clip element arm 20 is aligned over tapered surface 38. In this orientation, clip element arm 20 can be used as a lever arm to pry the clip element from the button element.

In another embodiment of the present invention, the clip element arm 20 is formed from a substantially flexible material, such that the orifice 26 of the clip element arm 20 is deformable. For example, the entire clip element arm 20 need not be manufactured from such a material if structural rigidity is required. Instead, only a portion of a surface of the clip element arm 20 adjacent the orifice 26 could be formed from such a flexible material. In any case, in operation, the orifice 26 of the clip element arm 20 is deformable or stretched to pass over the cap 16 of the button element 12. After passing over the cap 16 and positioned adjacent the shaft 14, the orifice 26 returns or reverts to its original shape around and adjacent the shaft 14. Further, as discussed above, and due to the relative sizing of the retention surface 36 and the orifice 26, once the orifice 26 returns to its original shape it is held in place (or held from detachment) by the retention surface 36. Further, the orifice 26 allows the clip element arm 20 to rotate around and about the shaft 14. In addition, this flexibility allows the patient or user to easily remove and reattach the clip element arm 20, which provides additional flexibility of movement and strap 108 adjustment.

It is envisioned that the clip element arm 20 can be manufactured from a variety of flexible and deformable materials. For example, the material may be silicone, a silicone-based material, a low-durometer silicone, an elastomeric material, a soft elastomer, thermoplastic elastomer or any combination thereof. The use of this flexible material also aids in providing a better seal with respect to the user's face A, as the attachment of the straps 108 to the buckle 28, and subsequent attachment of the clip element arm 20 to the button element 12, allows the flexible clip element arm 20 to stretch in a variety of directions based upon the direction that the straps 108 of the mask attachment assembly 104 are pulling. Further, the use of this flexible material allows the clip element arm 20 to be much more easily removed from the button element 12.

Figure 7:
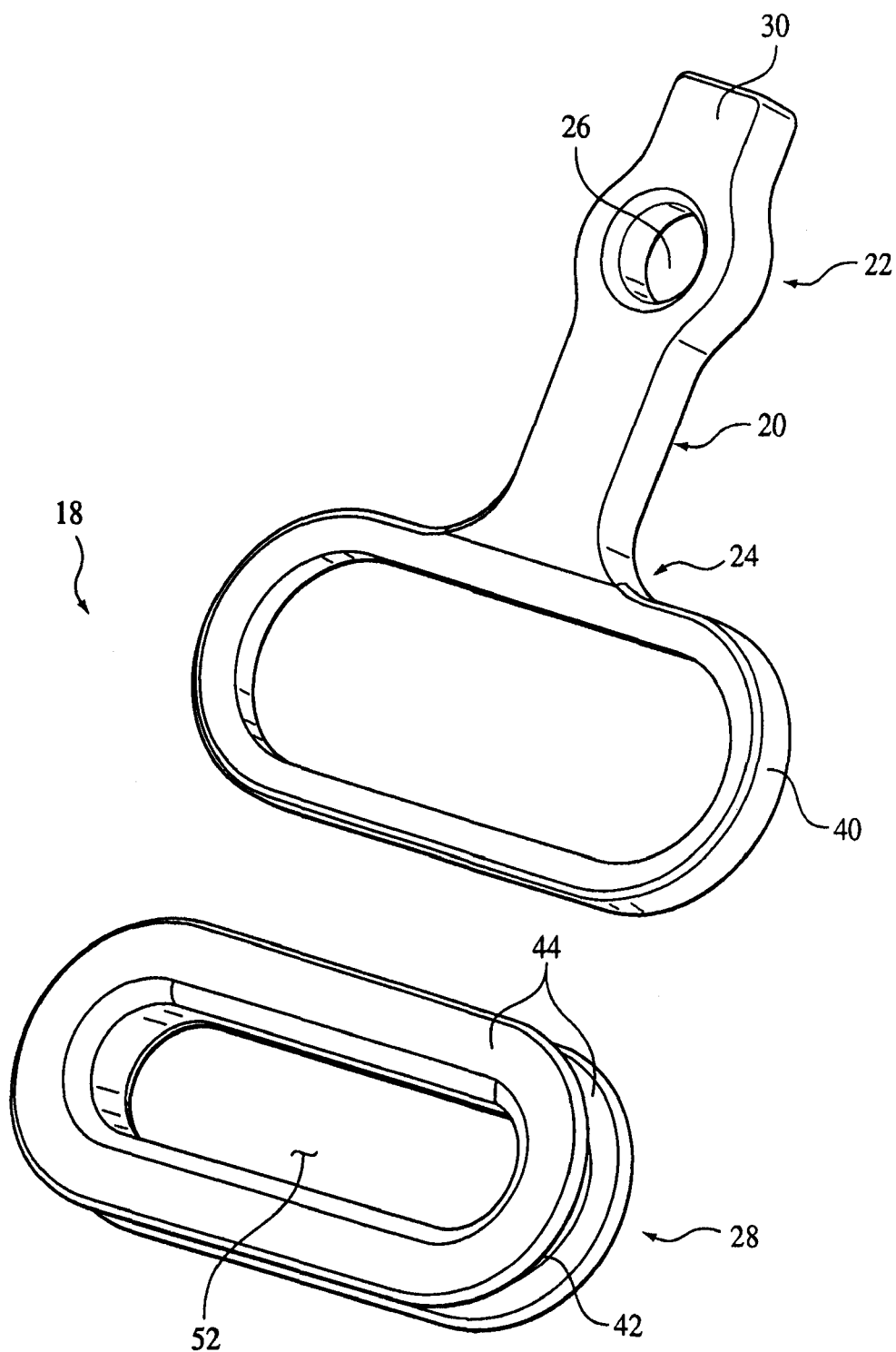
FIG. 7 is an exploded perspective view of one embodiment of a clip element of the mask mounting mechanism according to the principles of the present invention.
Figure 8:
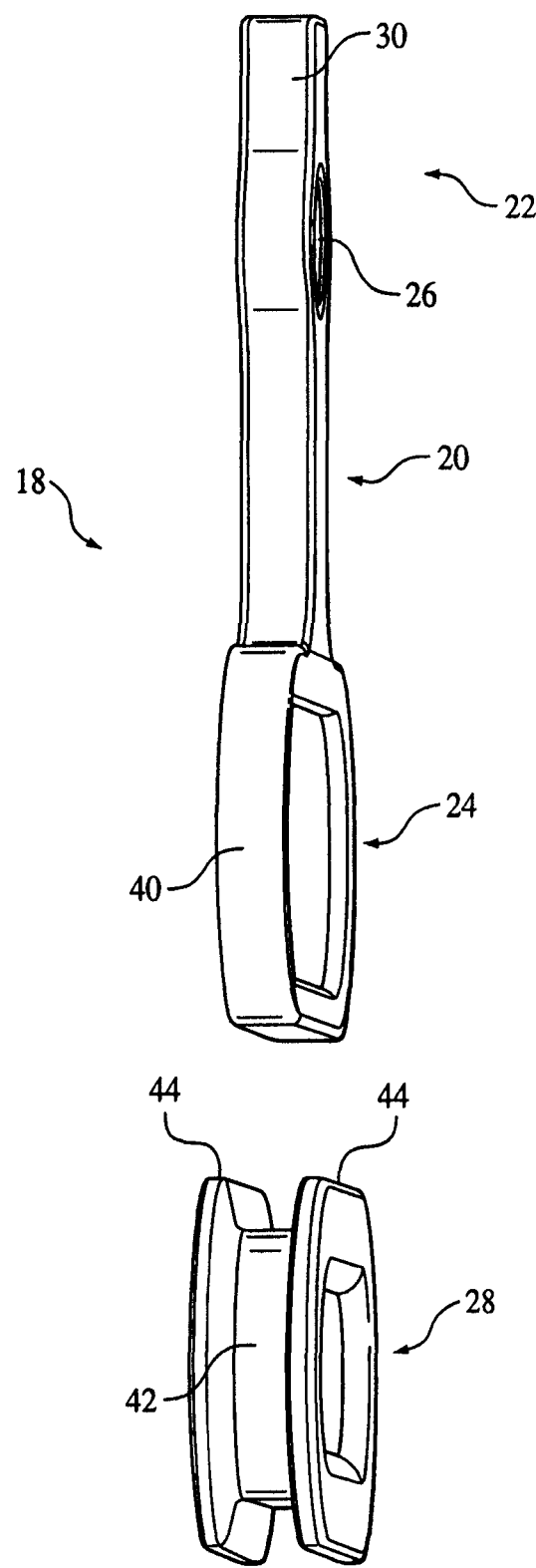
FIG. 8 is a further perspective view of the clip element of FIG. 7.

In another embodiment, the buckle 28 is removable from the first end 22 of the clip element arm 20. For example, as seen in FIGS. 7 and 8, the first end 22 of the clip element arm 20 may include a buckle loop 40. Further, the buckle 28 would include a buckle loop groove 42. In operation, the buckle loop 40 of the clip element arm 20 could be stretched and placed over the buckle loop groove 42. In this embodiment, the buckle 28 would be made from a rigid material, such that the buckle loop 40 could be easily stretched around and positioned within the buckle loop groove 42 of the buckle 28. In addition, walls 44 would form the buckle loop groove 42, and these walls 44 would ensure that the buckle loop 40 of the clip element arm 20 would not slide off of or otherwise disengage the buckle 28.

The use of a rigid buckle 28 would allow for a more effective attachment of the straps 108 of the mask attachment assembly 104 thereto. In particular, if the buckle 28 were manufactured from a flexible material, the tension on the straps 108 may overstretch and even break the flexible buckle 28, which is obviously an undesirable occurrence. Therefore, the use of a rigid material would prevent the straps 108 from overtorquing the buckle 28.

Figure 9:
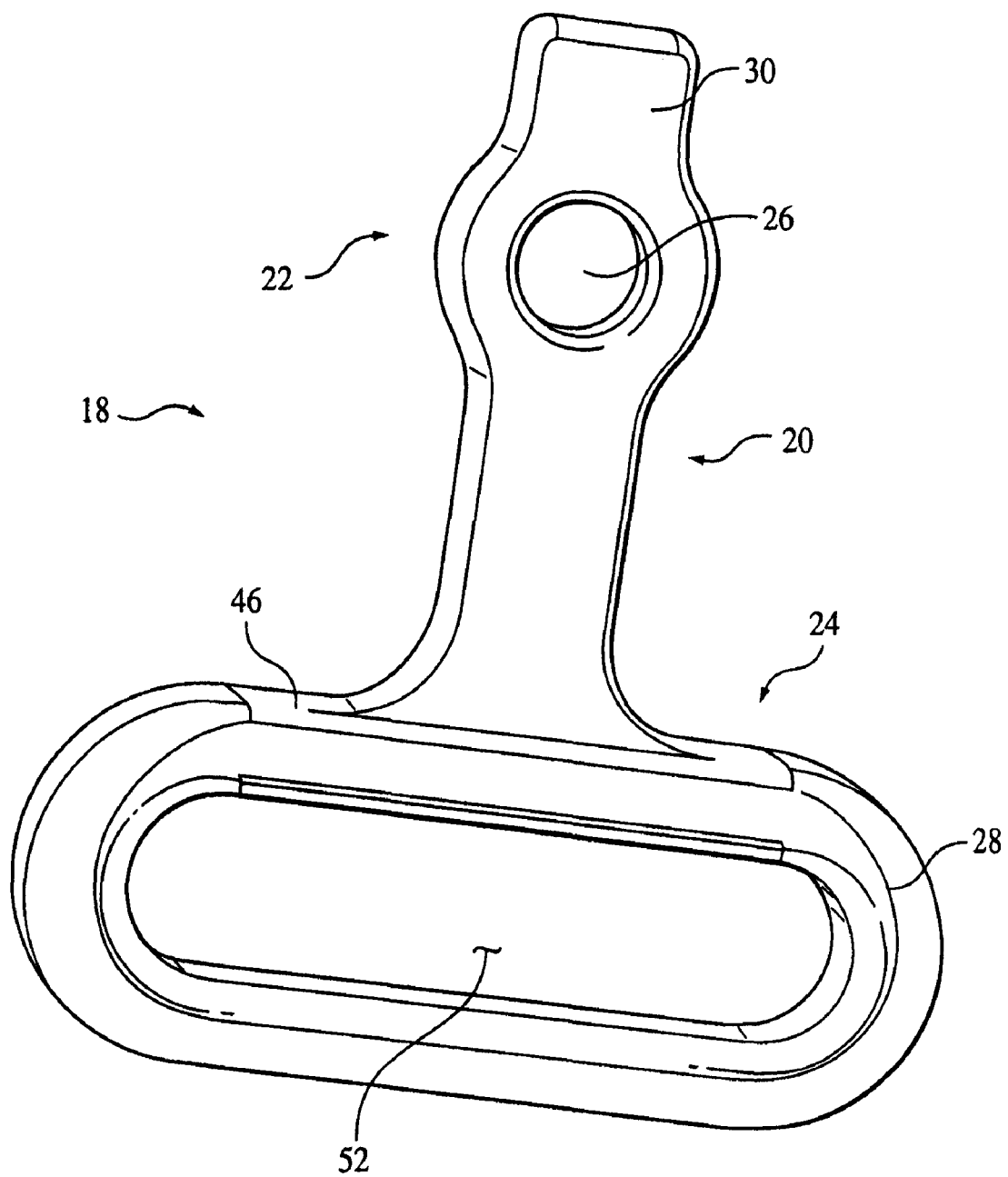
FIG. 9 is a perspective view of a further embodiment of a clip element of the mask mounting mechanism according to the principles of the present invention.

In another embodiment, and as illustrated in FIG. 9, as opposed to a flexible buckle loop 40, as in the previous embodiment, the first end 22 of the clip element arm 20 may include a clamp 46. This clamp 46 may be in the form of a C-shaped clamp or similar structure. Further, in such an embodiment, the clamp 46 portion of the clip element arm 20 may be formed of a rigid or semi-rigid material. For example, the buckle 28 could be snapped into or otherwise engaged with the clamp 46 of the clip element arm 20 in order to appropriately engage the buckle 28 with the clip element arm 20. Similar means for attaching the buckle 28 to the clip element arm 20 are envisioned.

Figure 10:
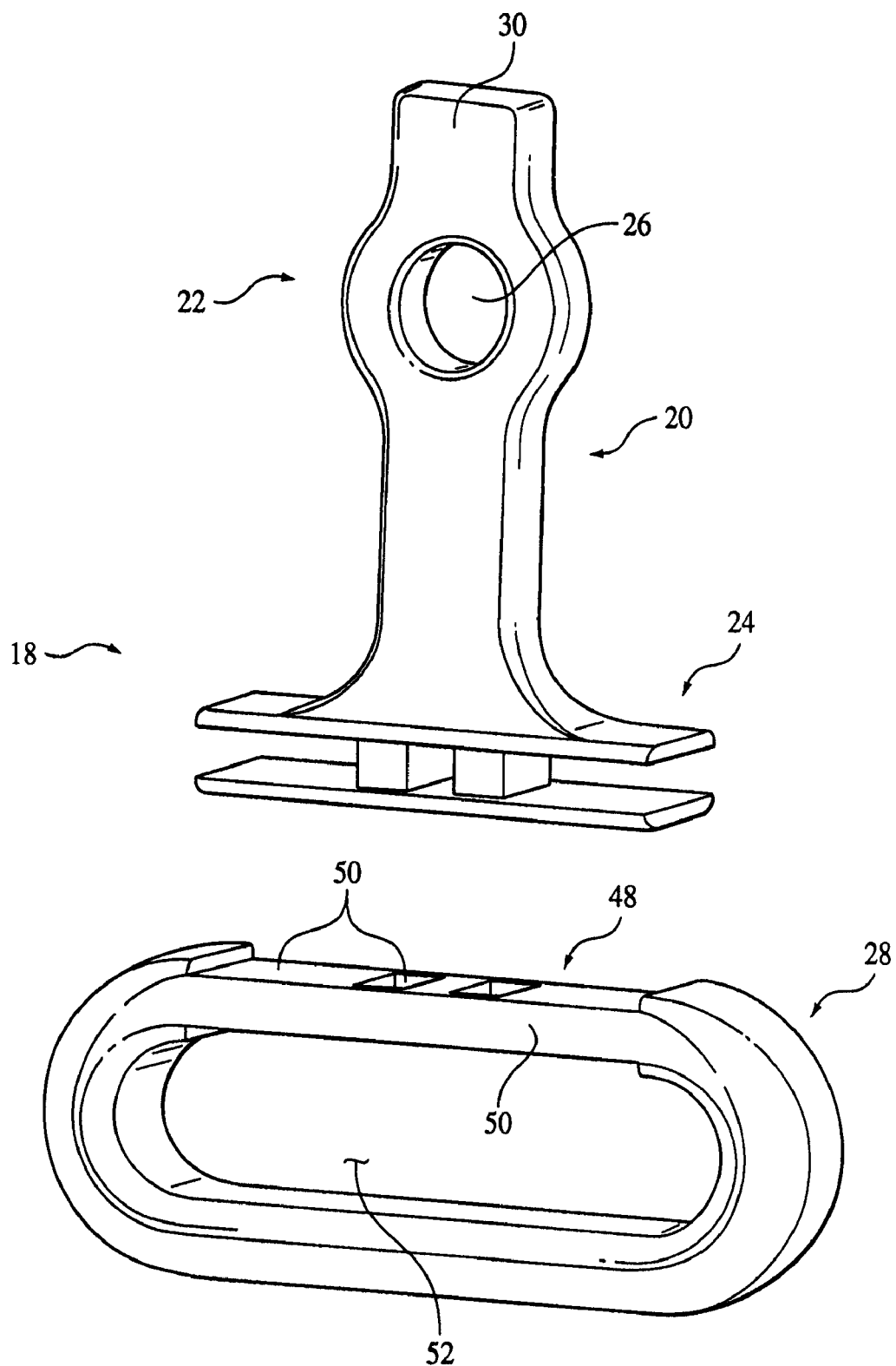
FIG. 10 is an exploded perspective view of yet another embodiment of a clip element of the mask mounting mechanism according to the principles of the present invention.

In another embodiment, the clip element arm 20 is formed from a substantially flexible material, and the first end 22 of the clip element arm 20 is molded over at least a portion of the buckle 28. For example, as best seen in FIG. 10, the buckle 28 may include a structure 48 including a plurality of contact surfaces 50. During the molding process, and as is known in the art, the first end 22 of the clip element arm 20 could be formed over the portion of the buckle 28, with the moldable material filling in and around and otherwise contacting the contact surfaces 50. Upon curing, the clip element arm 20 would be molded to the buckle 28. In this manner, the clip element arm 20 would be formed of a substantially flexible material, while the buckle 28 would be formed of a substantially rigid material. For example, such a rigid material could be a plastic, a rigid polymer, a molded material, a synthetic material, etc.

In another embodiment, the present invention is directed to the patient interface device 100, which includes the above-discussed mask 102 and mask attachment assembly 104. Further, the mask attachment assembly 104 would include one, and typically multiple straps 108. As described above, the mask mounting mechanism 10 would be used in connection with a mask wall 106 of the mask 102. Specifically, the button element 12 could be attached at various locations on the mask wall 106 for use in connection with the clip element 18. Various button elements 12 could be positioned in any number of places on the mask wall 106 to provide the user with a variety of attachment locations. Further, the button element 12 could be formed on any of the surfaces of the components and subcomponents of the patient interface device 100.

In one embodiment, the mask attachment assembly is at least a three-point attachment assembly, and at least one of the attachment points is at the buckle 28 of the clip element 18 of the mask mounting mechanism 10. In another embodiment, the patient interface device 100 includes the forehead contact member 110, such as illustrated in FIG. 1, and the button element 12 of the mask mounting mechanism 10 could extend from a wall or portion of the forehead contact member 110 for use in connection with the mask attachment assembly 104.

In this manner, the mask mounting mechanism 10 provides a flexible and rotatable clip element 18 for use in connection with a button element 12. As discussed above, the use of a flexible material, in combination with the tapered surface 38 and the tab 30, allows for the easy removal of the clip element 18 from the button element 12. Accordingly, removal of the clip element 18 (when at least one strap 108 is attached thereto) provides for the removal and/or release of the strap 108 from indirect attachment to the mask 102, the mask conduit coupling 112, the forehead contact member 110 or any combination thereof.

In operation, the user or patient can use the mask mounting mechanism 10 in connection with a variety of mask attachment assemblies 104 and associated masks 102. As opposed to being limited to a single type of mask attachment assembly 104, and also for providing the user with adjustability, such as when sleeping, and as discussed above, the clip element arm 20 is rotatable around the shaft 14 of the button element 12 to permit the use of different assemblies 104 or movement of the user while the patient interface device 100 is in use. Therefore, the user can use the mask mounting mechanism 10 of the present invention in connection with his or her preferred headgear or mask attachment assembly 104, provided the button element 12 is positioned at a preferred location on the mask wall 106 of the mask 102 or other assemblies or components of the patient interface device 100.

The pivotal nature of the clip element arm 20 allows for the adjustability of the direction that the clip element arm 20 extends from the mask 102. This may be particularly advantageous since these masks 102 are commonly used by users while they are sleeping. As is well known, a sleeping user may adjust the orientation of their head, which often results in modifying the forces exerted on the mask 102. The pivotable coupling permits the clip element arm 20 to be self-adjusting, as the forces exerted on the mask 102 change without requiring user manipulation. When the user moves his or her head, the flexible nature of the clip element arm 20, coupled with the rotatability of the clip element arm 20 about the shaft 14 allows the clip element to self adjust to reach an orientation that equalizes the forces exerted on the clip element, thereby minimizing, discomfort, or strap 108 disengagement, which in turn could potentially result in breaking the seal between the mask 102 and the user's face A.

Due to the rotatability of the clip element arm 20 about the shaft 14, one skilled in the art can best appreciate that the arm 20 is therefore capable of extending in a variety of different orientations in order to apply the moment in a desirable direction to enhance the seal created with the user's face A and maximize comfort. In other applications, a poor seal may occur in other regions about the mask 102 due to the user's unique facial characteristics or the particular design of the mask 102. The inventors of the present invention contemplate that the clip element arm 20 may be directed in a variety of other directions via the straps 108 in order to enhance the seal integrity regardless of the particular region in which the seal integrity has become compromised. For instance, in the event that the seal has become compromised at the interface between the user's cheeks and mask 102, the straps 108 could be adjusted, and the clip element arms 20 could be directed laterally rather than downwardly.

In this manner, the present invention provides a mask mounting mechanism 10 that can be used in connection with a patient interface device 100, and the clip element 18 is easily attachable to and removable from the button element 12. In addition, the clip element 18 is continuously rotatable around the shaft 14 of the button element 12 due to the shapes and sizes of the subcomponents. Still further, when the clip element arm 20 is manufactured from a substantially flexible material, such as a thermoplastic elastomer, the orifice 26 of the clip element arm 20 is stretched and deformed over the cap 16 of the button element 12, and the orifice 26 returns to its original shape and is thus retained by the retention surface 36 of the cap 16.

The mask mounting mechanism 10 and patient interface device 100 of the present invention provides full rotatability and adjustability of the mask attachment assembly 104, and further provides this flexibility of adjustment and movement without jeopardizing the seal between the mask 102 and the user's face A. The flexible clip element arm 20 is also capable of bending in various angles and directions, which may follow the direction of the straps 108 of the mask attachment assembly 104. Accordingly, there is no preset or predetermined position of the clip element arm 20, since, in one preferred embodiment, the arm 20 is fully flexible and rotatable. Further, the mask mounting mechanism 10 of the present invention allows a patient wearing the mask 102 much more flexibility of movement.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A mask mounting mechanism for use in connection with a patient interface device having a mask and a mask attachment assembly having at least one strap and configured to retain the mask in a sealed position on a user's face, the mask mounting mechanism comprising:
   at least one button element extending from a wall of the mask, the button element including a shaft and a cap having a diameter greater than the diameter of the shaft; and
   a clip element, including a clip element arm having a first end and a second end with an orifice extending therethrough, wherein the orifice has a second diameter that is smaller than the diameter of the cap and wherein the clip element is engageable with the button element by engaging the orifice of the clip element arm over the cap and adjacent the shaft of the button element; and wherein the clip element is continuously rotatable around the shaft of the button element responsive to the shaft being received through the orifice and the orifice adjacent the shaft.

2. The mask mounting mechanism of claim 1, further comprising a tab extending from the clip element arm and configured to be grasped by a user to disengage the clip element from the button element.

3. The mask mounting mechanism of claim 2, wherein the tab portion further comprises at least one ridge extending from a surface of the tab portion and providing a gripping surface for the user to grasp the tab portion.

4. A mask mounting mechanism for use in connection with a patient interface device having a mask and a mask attachment assembly having at least one strap and configured to retain the mask in a sealed position on a user's face, the mask mounting mechanism comprising:
   at least one button element extending from a wall of the mask, the button element including a shaft and a cap having a diameter greater than the diameter of the shaft; and
   a clip element, including a clip element arm having a first end and a second end with an orifice extending therethrough wherein, the clip element is engageable with the button element by engaging the orifice of the clip element arm over the cap and adjacent the shaft of the button element; and wherein the clip element is continuously rotatable around the shaft of the button element, wherein at least a portion of the clip element arm adjacent the orifice is formed from a substantially flexible material, such that, in operation, the orifice extending through the clip element arm is deformable to pass over the cap of the button element and reverts substantially to its original shape around and adjacent the shaft of the button element.

5. The mask mounting mechanism of claim 4, wherein the flexible material is selected from the group comprising a silicone, a silicone-based material, a low-durometer silicone, an elastomeric material, a soft elastomer and a thermoplastic elastomer.

6. The mask mounting mechanism of claim 1, wherein the diameter of the orifice of the clip element arm is greater than the diameter of the shaft of the button element, such that, when the clip element arm is attached to the button element, the clip element arm is rotatable about the shaft.

7. The mask mounting mechanism of claim 1, wherein the buckle of the clip element is formed from a substantially rigid material.

8. The mask mounting mechanism of claim 1, wherein the clip element arm further includes a buckle attached to the first end of the clip element arm and configured to engage the at least one strap of the mask assembly.

9. A mask mounting mechanism for use in connection with a patient interface device having a mask and a mask attachment assembly having at least one strap and configured to retain the mask in a sealed position on a user's face, the mask mounting mechanism comprising:
   at least one button element extending from a wall of the mask, the button element including a shaft and a cap having a diameter greater than the diameter of the shaft; and
   a clip element, including a clip element arm having a first end and a second end with an orifice extending therethrough wherein, the clip element is engageable with the button element by engaging the orifice of the clip element arm over the cap and adjacent the shaft of the button element; wherein the clip element is continuously rotatable around the shaft of the button element, wherein the buckle of the clip element is formed from a substantially rigid material, and wherein the clip element arm is formed from a substantially flexible material, and at least a portion of the first end of the clip element arm is molded over at least a portion of the buckle.

10. The mask mounting mechanism of claim 1, wherein the cap of the button element is substantially in the form of a mushroom, a cone or any combination thereof.

11. The mask mounting mechanism of claim 4, wherein the cap of the button element further comprises a retention surface configured to retain the clip element arm after engagement of the clip element with the button element.

12. The mask mounting mechanism of claim 11, wherein at least a portion of the retention surface is tapered to provide a less obstructed deformation and removal of the clip element orifice from around the shaft and over the cap.

13. A patient interface device, comprising:
   a mask having a mask wall with a mask port extending therethrough;
   a mask conduit coupling in fluid communication with the mask port;
   a mask attachment assembly having at least one strap; and
   a mask mounting mechanism, including:
      (i) at least one button element extending from the mask wall, a wall of the mask conduit coupling or any combination thereof, the button including a shaft and a cap having a diameter greater than the diameter of the shaft; and
      (ii) a clip element, including:
         (1) a clip element arm having a first end and a second end with an orifice extending therethrough wherein the orifice has a second diameter that is smaller than the diameter of the cap; and
         (2) a buckle attached to the first end of the clip element and configured to engage the at least one strap of the mask attachment assembly;
      wherein, the clip element is engageable with the button element by engaging the orifice of the clip element arm over the cap and adjacent the shaft of the button element; and
      wherein the clip element is continuously rotatable around the shaft of the button element when the shaft is received through the orifice and the orifice is adjacent the shaft.

14. The patient interface device of claim 13, wherein the mask attachment assembly is at least a three-point attachment assembly, wherein at least one of the attachment points is at the buckle of the clip element of the mask mounting mechanism.

15. The patient interface device of claim 13, further comprising a forehead contact member, wherein at least a portion of the forehead contact member is configured to contact at least a portion of a user's forehead.

16. The patient interface device of claim 15, wherein the button element of the mask mounting mechanism extends from a wall of the forehead contact member.

17. The patient interface device of claim 13, wherein the mask is a nasal mask, a nasal and oral mask, a mouth mask, a full-face mask or any combination thereof.

18. The patient interface device of claim 13, wherein the mask conduit coupling has a first end and a second end, wherein the first end of the mask conduit coupling is attached to the mask, and the second end of the mask conduit coupling is in fluid communication with a patient circuit, a conduit, a pressure support device, a gas source or any combination thereof.

19. The patient interface device of claim 13, wherein the at least one strap of the mask attachment assembly is adjustable.

20. The patient interface device of claim 13, wherein the at least one strap of the mask attachment assembly is attached to the buckle of the clip element, such that removal of the clip element from the button element releases the at least one strap from indirect attachment to the mask, the mask conduit coupling, a forehead contact member or any combination thereof.

* * * * *